(12) United States Patent
Carli

(10) Patent No.: US 7,306,604 B2
(45) Date of Patent: Dec. 11, 2007

(54) CLAMPING NUT FOR AN OSTEOSYNTHESIS DEVICE

(75) Inventor: Olivier Carli, Geneva (CH)

(73) Assignee: Scient'X, Guyancourt (FR)

( * ) Notice: Subject to any disclaimer, the term of this patent is extended or adjusted under 35 U.S.C. 154(b) by 482 days.

(21) Appl. No.: 10/427,950

(22) Filed: May 2, 2003

(65) Prior Publication Data

US 2004/0092938 A1     May 13, 2004

(30) Foreign Application Priority Data

Nov. 8, 2002    (FR)    ................................ 02 14038

(51) Int. Cl.
    *A61B 17/56*    (2006.01)
(52) U.S. Cl. ............................. 606/61; 411/27; 411/222
(58) Field of Classification Search ................. 606/61, 606/66, 56, 59, 72; 411/432, 380, 537, 27, 411/222; 384/104, 108, 498, 205, 549; 623/17.14; 403/21, 22, 112, 113
    See application file for complete search history.

(56) References Cited

U.S. PATENT DOCUMENTS

| | | | | |
|---|---|---|---|---|
| 1,298,308 A | * | 3/1919 | Dodds | ..................... 411/372.6 |
| 2,875,002 A | * | 2/1959 | McDaniel | ................... 384/205 |
| 3,135,154 A | * | 6/1964 | Zenzic | ......................... 411/12 |
| 4,140,413 A | * | 2/1979 | Conrad | ....................... 403/370 |
| 5,147,363 A | | 9/1992 | Harle | |
| 5,151,103 A | | 9/1992 | Tepic et al. | |
| 5,486,174 A | * | 1/1996 | Fournet-Fayard et al. | .... 606/61 |
| 5,501,684 A | * | 3/1996 | Schlapfer et al. | ............. 606/73 |
| 5,746,741 A | * | 5/1998 | Kraus et al. | .................. 606/54 |
| 5,902,303 A | * | 5/1999 | Eckhof et al. | ................ 606/50 |
| 6,139,549 A | * | 10/2000 | Keller | .......................... 606/61 |
| 6,287,309 B1 | * | 9/2001 | Baccelli et al. | ............... 606/61 |

FOREIGN PATENT DOCUMENTS

| | | |
|---|---|---|
| DE | 29522089 | 8/1999 |
| EP | 0933065 | 8/1999 |
| EP | 0997107 | 5/2000 |
| WO | 9841160 | 9/1998 |

* cited by examiner

*Primary Examiner*—Brian E. Pellegrino
(74) *Attorney, Agent, or Firm*—Dennison, Schultz & MacDonald

(57) ABSTRACT

A clamping nut suitable for co-operating with a threaded shank of an osteosynthesis appliance, the nut including an annular body and a tapped bore for cooperating with the threaded shank. The annular body is provided with a structure which enables turning the body and with a transverse bearing face. The osteosynthesis nut further includes a ring mounted in a housing of the annular body which is provided internally with the tapped bore, and which cooperates externally with the annular body.

10 Claims, 3 Drawing Sheets

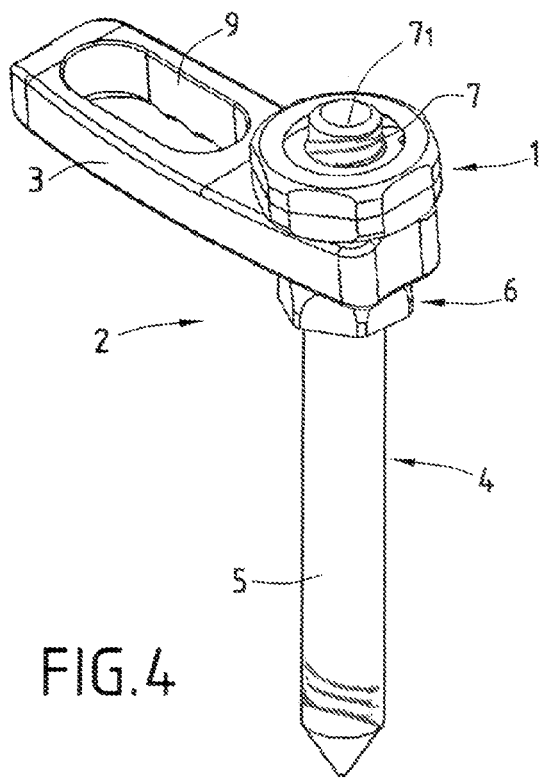
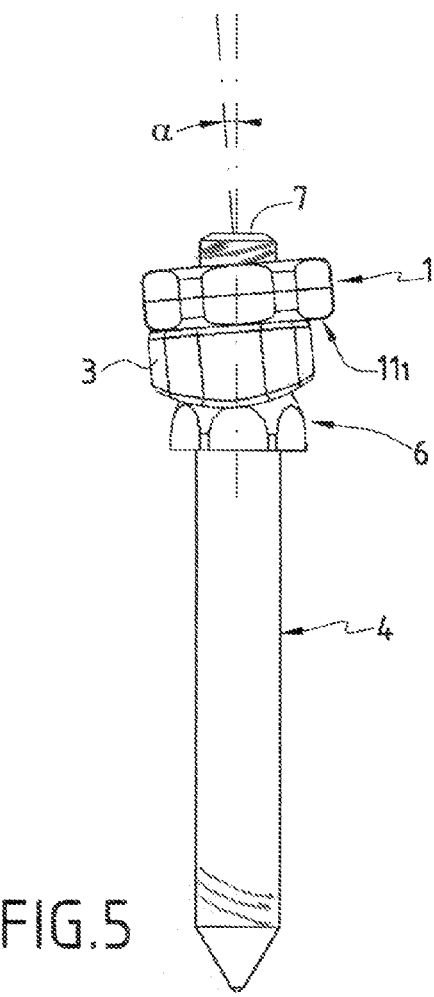
FIG.4
FIG.5

CLAMPING NUT FOR AN OSTEOSYNTHESIS DEVICE

The present invention relates to the technical field of osteosynthesis, in particular of the spine, and it relates more particularly to a clamping nut used in osteosynthesis devices for the spine.

More precisely, the invention provides a clamping nut designed to present an angle relative to an osteosynthesis appliance in the general sense.

BACKGROUND OF THE INVENTION

One of the known applications for the invention relates to devices designed to correct and hold a set of vertebrae in a determined position. In this application, such a device comprises an intervertebral connection element such as a plate or a rod suitable for being held in position by bone anchor elements such as screws implanted in the vertebrae. Each bone anchor element is provided with a head, and a threaded shank for mounting the plate which has through holes. The plate is engaged on the threaded shank via a through hole and the portion of the shank that projects from the plate is used for receiving a clamping nut.

Given the anatomy of the vertebrae, it is necessary to allow for an adaptable relative angle to exist between the anchor screw and the intervertebral connection element. In order to allow for such an adaptable relative angle, it is known to fit anchor screws with a spherical joint for receiving the intervertebral connection element. Such a spherical joint is arranged between the anchor screw and the threaded shank in order to enable the threaded shank receiving the intervertebral connection element to take up orientations in a plurality of different directions.

Although an anchor screw of the type having a spherical joint makes it possible to achieve an adaptable relative angle between said screw and the intervertebral connection element, it must be considered that making a spherical joint on an anchor screw contributes to weakening it by including a moving interface that can even lead to the intervertebral connection element breaking. Furthermore, it has been found that even in the presence of an anchor screw of the type having a spherical joint, the threaded shank does not always extend to project perpendicularly relative to the intervertebral connection element, given the anatomy of the vertebrae and the zone in which the anchor screw is implanted. It follows that the nut for screwing onto the threaded shank can no longer be tightened properly, insofar as the intervertebral connection element does not extend perpendicularly to the threaded shank, such that the intervertebral connection element is subjected to inappropriate stresses and cannot be completely prevented from moving, at least not with appropriate clamping force.

OBJECT AND SUMMARY OF THE INVENTION

The object of the present invention is thus to remedy the above-specified drawbacks by proposing a technique enabling an intervertebral connection element to be blocked effectively in position on an osteosynthesis appliance, regardless of the relative angle between them.

The object of the invention is thus to provide a clamping nut capable of adapting to the relative angle between the threaded shank of an osteosynthesis appliance and an intervertebral connection element.

To achieve such an object, the clamping nut comprises an annular body and a tapped bore for co-operating with the threaded shank, the annular body being provided with turning means and with a transverse bearing face. According to the invention, the nut further comprises:
- a ring mounted in a housing of the annular body and provided internally with the tapped bore, and co-operating externally with the annular body to form a spherical joint; and
- means for preventing relative turning between the ring and the annular body.

According to a preferred implementation characteristic, the ring is provided externally with a ball-surface co-operating with the housing of complementary shape in order to form the spherical joint.

According to another characteristic of the invention, the means for preventing relative turning are formed by two studs extending in diametrically opposite directions from the outside of the ring or of the annular body, each stud being received in a cavity formed in the annular body or in the ring.

According to another characteristic of the invention, the cavities and the studs are dimensioned in such a manner as to allow the spherical joint between the annular body and the ring to rock.

According to a preferred embodiment characteristic, the annular body is constituted by two annular half-bodies holding the ring captive and positioned relative to each other by means of at least one centering peg, being fixed together with the help of assembly means.

According to another preferred embodiment characteristic, the turning means are constituted by flats arranged on the annular body which presents a hexagonal or other section.

The invention also provides an osteosynthesis device comprising:
- at least one osteosynthesis appliance presenting a threaded shank;
- an intervertebral connection element provided with a passage for receiving the threaded shank; and
- at least one clamping nut screwed onto the threaded shank in such a manner that its transverse bearing face comes into contact with the intervertebral connection element.

BRIEF DESCRIPTION OF THE DRAWINGS

Various other characteristics appear from the following description made with reference to the accompanying drawings, which show embodiments of the invention as non-limiting examples.

FIGS. 4 and 5 are respectively a perspective view and an elevation view showing an osteosynthesis device using a clamping nut in accordance with the invention.

MORE DETAILED DESCRIPTION

Figure 1:
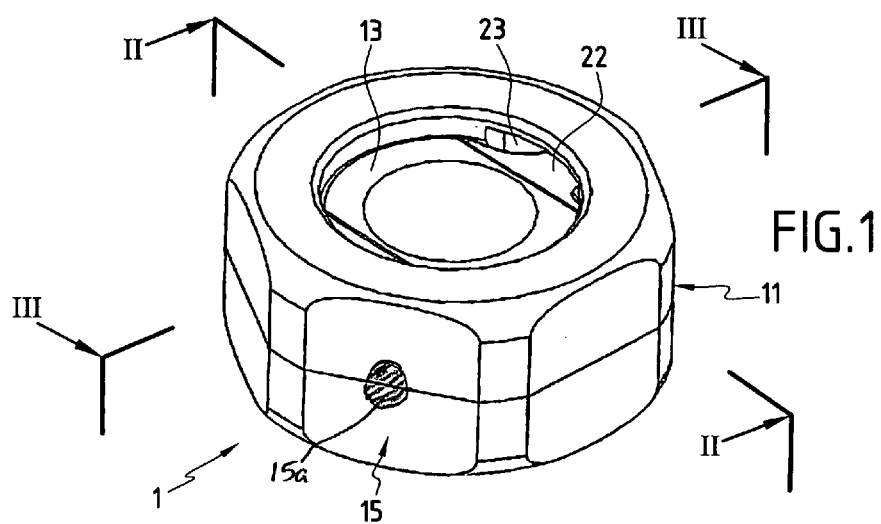
FIG. 1 is a perspective view showing an embodiment of the clamping nut in accordance with the invention.
Figure 2:
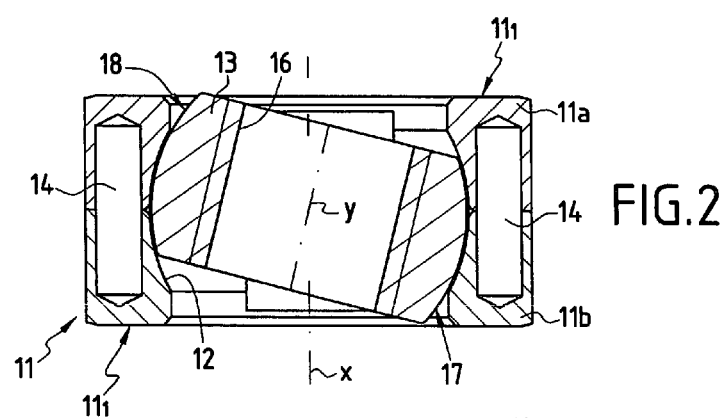
FIGS. 2 and 3 are cross-section views taken respectively on lines II-II and III-III of FIG. 1.
Figure 3:
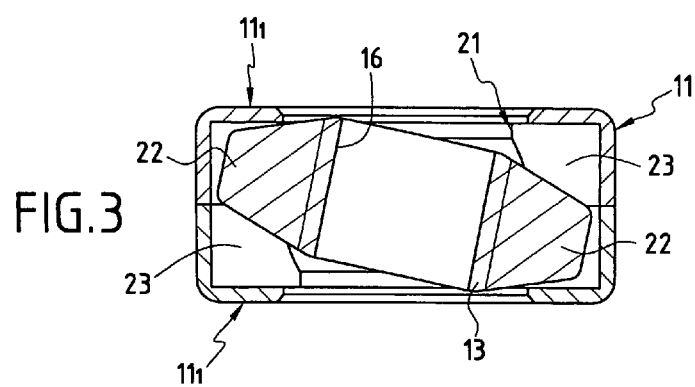

FIGS. 1 to 3 show a clamping nut 1 in accordance with the invention for use in an osteosynthesis device 2 for the spine.

In the example shown in FIGS. 4 and 5, the osteosynthesis device 2 comprises an intervertebral connection element 3 such as a plate in the example shown together with at least one osteosynthesis appliance 4 in the general sense capable of being made in various known ways. The osteosynthesis appliance 4 thus constitutes, for example, a bone anchor element in the form of a hook or as shown in the drawings, in the form of an anchor screw. Such an osteosynthesis appliance 4 can also be in the form of a plate or of an intermediate connection element.

In the example shown, the osteosynthesis appliance 4 forming a bone anchor screw comprises a threaded portion 5 and a head 6 from which there extends a threaded shank 7. In the example shown, the threaded shank 7 extends substantially in line with the threaded portion 5. In known manner, the intervertebral connection element 3 is provided with one hole or passage 9, or more generally with a plurality of holes or passages 9. Each hole 9 serves to pass the threaded shank 7 so that a portion thereof projects from the intervertebral connection element 3 in order to enable the clamping nut 1 of the invention to be screwed thereon.

As can be seen more precisely in FIGS. 1 to 3, the clamping nut 1 of the invention comprises an annular body 11 internally defining a housing 12 for receiving a ring 13. The annular body 11 thus possesses an axis of revolution or symmetry x which extends in a direction that is substantially perpendicular relative to the transverse faces $11_1$ of the annular body. It should be observed that one of the transverse faces $11_1$ constitutes a bearing face that is to come into contact with the intervertebral connection element 3.

In a preferred embodiment, the annular body 11 is constituted by two annular half-bodies 11a, 11b that hold the ring 13 captive, the half-bodies being positioned relative to each other by means of at least one centering peg 14, there being two such pegs in the example shown. The two annular half-bodies 11a, 11b are fixed together with the help of any type of assembly means, for example by welding.

The annular body 11 is provided with turning means 15 enabling it to be turned. In a preferred embodiment, the turning means 15 are constituted by flats provided on the annular body which thus presents a section that is hexagonal, for example. Naturally, the turning means 15 can be made in other ways, for example by means of holes 15a for receiving a driving implement.

In accordance with the invention, the inside of the ring 13 is provided with a tapped bore 16 suitable for co-operating with the threaded shank 7 of an osteosynthesis device 4. The threaded bore 16 thus possesses an axis of symmetry y.

According to an advantageous characteristic of the invention, the ring 13 and the annular body 13 are adapted in such a manner as to co-operate to constitute a spherical joint assembly 17 enabling the ring 13 to be angled so that there is a relative angle between the axis y of the ring and the axis x of the annular body 11. In the example shown, the ring 13 is provided on the outside with a ball-surface 18 co-operating with the housing 12 of complementary shape presented by the annular body 11. As can be seen more clearly in FIG. 2, the outside surface of the ring 13 thus presents a segment of a sphere 18 suitable for co-operating with a complementary segment of a sphere defining part of the housing 12 in the annular body.

In the example shown, the ring 13 is provided with a ball-surface 18 presenting a convex spherical surface while the housing 12 possesses a concave surface. Naturally, it would be possible to interchange the concave and convex shapes between the ring 13 and the annular body 11.

According to another characteristic of the invention, the clamping nut 1 has means 21 ensuring that the ring 13 and the annular body 11 are constrained to turn together. The means 21 prevent the ring 13 from turning about its axis y relative to the annular body 11. In the embodiment shown, these blocking means 21 are in the form of two lugs or studs 22 extending in diametrically opposite manner from the outside of the ring 13. Each stud 22 is received in a cavity 23 formed in the annular body 11. Naturally, the cavities 23 and the studs 22 are dimensioned so as to provide a spherical joint between the annular body 11 and the ring 13. Naturally, it would be possible to devise studs 22 projecting from the annular body 11 to co-operate with cavities 23 formed in the ring 13.

The clamping nut 1 of the invention possesses the advantage of presenting an adaptable relative angle between the axis of the tapped ring 13 and the annular body 11, i.e. more precisely one of its transverse bearing faces $11_1$. The advantage of the clamping nut 1 of the invention can be seen clearly in FIG. 5 which shows an intervertebral connection plate 3 inclined at an angle α relative to the threaded shank 7. Screwing the tapped ring 13 onto the threaded shank 7 leads to the bearing face $11_1$ of the annular body 11 coming into contact with the plate 3. Given the presence of a spherical joint between the tapped ring 13 and the annular body 11, the transverse face $11_1$ of the annular body comes into contact with the plate 3 and then presses against it over its entire area. The clamping force of the nut is thus under good control and the plate 3 is not subjected to unsuitable stresses.

Figure 6:
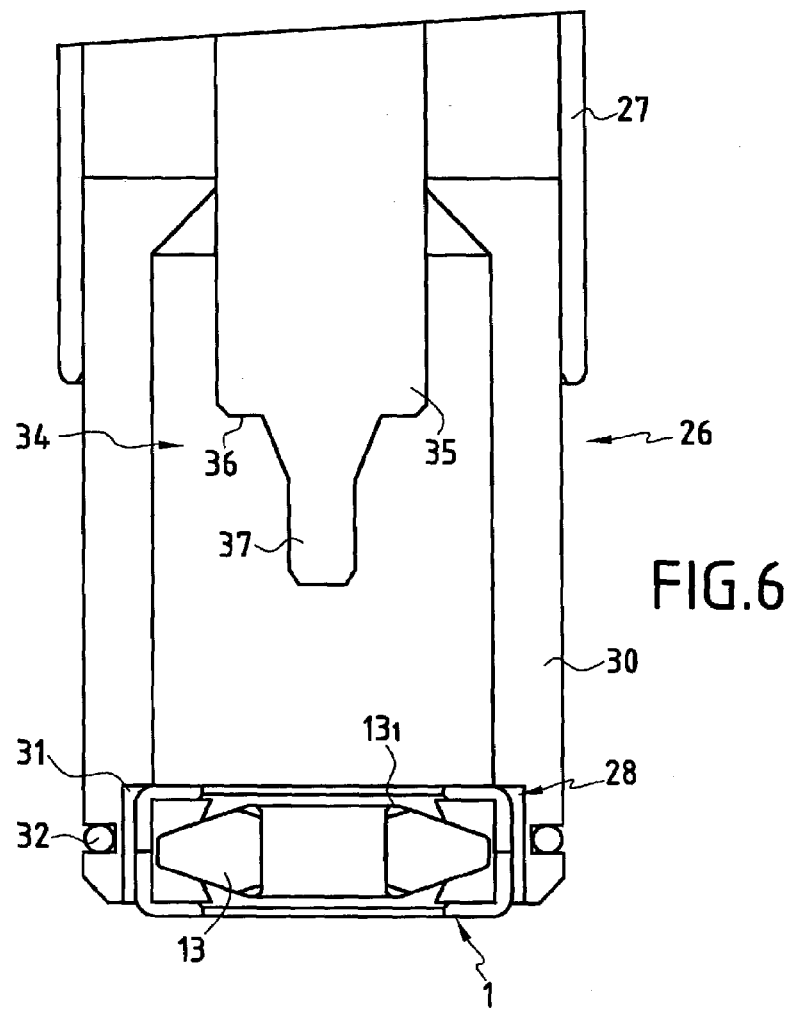
FIGS. 6 and 7 are elevation views showing two characteristic positions of an instrument for providing help in mounting a nut in accordance with the invention.
Figure 7:
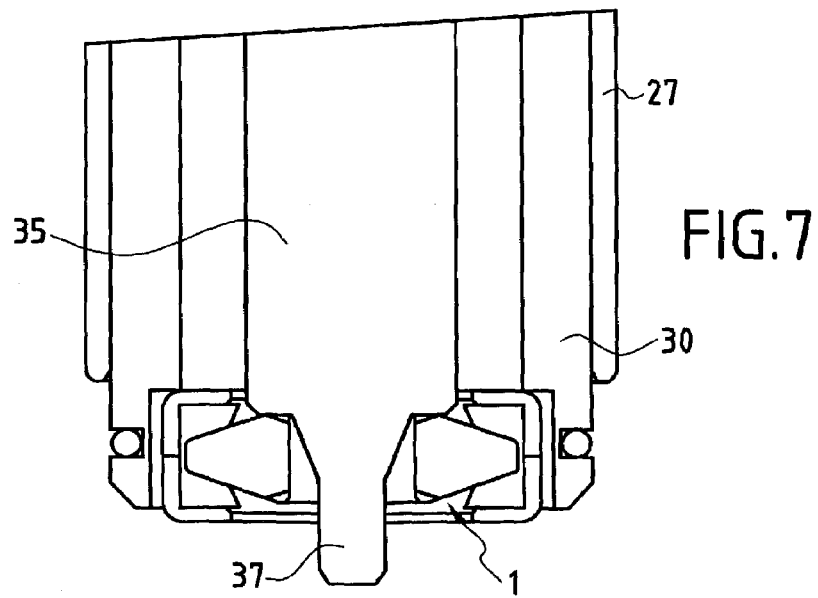

FIGS. 6 and 7 show an embodiment of an instrument 26 for providing assistance in mounting the clamping nut 1 of the invention on the threaded shank 7 that projects from the intervertebral connection element 3. The instrument 26 is in the form of an elongate body 27 provided with a handle (not shown).

The instrument 26 includes means 28 enabling it to take hold of the clamping nut 1. In the embodiment shown, these holding means 28 are provided by a sheath 30 carried by the body 27 and defining at the end thereof a cavity 31 for receiving the mounting nut 1, being of a shape that is complementary to the shape of the mounting nut. In addition, a resilient member 32 projecting into the cavity 31 serves to hold the nut in a reliable position inside the sheath 30.

The instrument 26 also has means 34 for temporarily preventing the spherical joint 17 in the mounting nut 1 from moving. These means 34 enable the ring 13 to be maintained in a fixed position thus making it easier to screw onto the threaded shank 7. In the embodiment shown, the means 34 for temporarily preventing movement of the nut are implemented by a moving rod 35 designed to press against the ring 13 so as to keep it stationary relative to the annular body 11. As can be seen in FIGS. 6 and 7, the moving rod 35 is provided with a bearing surface 36 for coming into contact with a transverse face $13_1$ of the ring 13.

According to a preferred embodiment characteristic, the moving rod 35 for pressing against the ring is extended by an insertion nose 37, which nose passes through the tapped bore 16 while the moving rod is pressing against the ring 13, thus penetrating into a recess $7_1$ formed in the end of the threaded shank 7.

In order to mount the clamping nut 1 on the threaded shank 7, the bearing rod 35 is moved so as to bear against the tapped ring 13, thus making it easier to position the ring relative to the threaded shank 7. Thereafter the bearing rod 35 is retracted to enable the tapped ring to be screwed onto the threaded shank 7.

The invention is not limited to the examples described and shown since various modifications can be made thereto without going beyond its ambit.

What is claimed is:

1. A clamping nut suitable for co-operating with a threaded shank of an osteosynthesis appliance, the nut comprising:
    an annular body comprising an outer face and a housing therein and provided with means for turning the annular body on the outer face comprising flat faces or recesses which interact with a driving implement, and with a transverse bearing face;
    a ring mounted in the housing of the annular body, the ring being provided internally with a tapped bore for cooperating with the threaded shank, and means for cooperating externally with the annular body to form a spherical joint; and
    means interposed between the ring and the annular body for preventing relative movement between the ring and the annular body upon turning of the annular body.

2. A clamping nut according to claim 1, wherein the ring is provided externally with a ball-surface co-operating with the housing of complementary shape in order to form the spherical joint.

3. A clamping nut according to claim 1, wherein the means for preventing relative turning comprises two studs extending in diametrically opposite directions from the annular body or from the outside of the ring or two studs received in a cavity formed in the ring or in the annular body.

4. A clamping nut according to claim 3, wherein the cavities and the studs are dimensioned in such a manner as to allow the spherical joint between the annular body and the ring to rock.

5. A clamping nut according to claim 1, wherein the annular body is comprises two annular half-bodies holding the ring captive and positioned relative to each other by means of at least one centering peg, being fixed together with assembly means.

6. A clamping nut according to claim 1, wherein the turning means are constituted by flats arranged on the annular body which presents a section that is hexagonal.

7. An osteosynthesis device comprising:
    at least one osteosynthesis appliance presenting a threaded shank;
    an intervertebral connection element provided with a passage for receiving the threaded shank; and
    at least one clamping nut according to claim 1 screwed onto the threaded shank in such a manner that its transverse bearing face is in contact on the intervertebral connection element.

8. In combination, a clamping nut according to claim 1, and an instrument for providing assistance in mounting the clamping nut on the threaded shank of an osteosynthesis appliance, the instrument including: means for holding the clamping nut; and blocking means for temporarily preventing the spherical joint from moving.

9. A combination according to claim 8, wherein the blocking means comprises a rod movable to bear against the ring of the clamping nut.

10. A combination according to claim 9, wherein the movable rod for bearing against the ring is extended by an insertion nose for passing through the tapped bore of the ring in order to penetrate into a recess provided at the end of the threaded shank.

* * * * *